United States Patent [19]

Sickler

[11] Patent Number: 5,267,857
[45] Date of Patent: Dec. 7, 1993

[54] BRIGHTNESS CONTROL SYSTEM FOR DENTAL HANDPIECE LIGHT

[75] Inventor: Robert L. Sickler, Aloha, Oreg.

[73] Assignee: A-Dec, Inc., Newberg, Oreg.

[21] Appl. No.: 17,135

[22] Filed: Feb. 12, 1993

[51] Int. Cl.$^5$ ............................. A61C 1/00; A61C 1/02
[52] U.S. Cl. ................................... 433/29; 433/28
[58] Field of Search .................... 433/27, 28, 29, 98

[56] References Cited

U.S. PATENT DOCUMENTS

| | | | |
|---|---|---|---|
| 2,539,828 | 1/1951 | Goldis et al. | 240/2.18 |
| 3,590,232 | 6/1971 | Sedowski | 240/2 |
| 3,634,938 | 5/1989 | Hutchinson | 433/29 |
| 4,053,756 | 10/1977 | Takahashi | 362/7 |
| 4,060,724 | 11/1977 | Heine et al. | 362/32 |
| 4,082,961 | 4/1978 | Genuit | 207/141 |
| 4,117,597 | 10/1978 | Trist et al. | 32/27 |
| 4,171,572 | 10/1979 | Nash | 32/27 |
| 4,330,274 | 5/1982 | Friedman et al. | 433/29 |
| 4,334,863 | 6/1982 | Magid et al. | 433/29 |
| 4,826,431 | 5/1989 | Fujimura et al. | 433/29 |
| 4,886,452 | 12/1989 | Löhn | 433/32 |
| 4,902,225 | 2/1990 | Löhn | 433/80 |
| 4,975,058 | 12/1990 | Woodward | 433/126 |

OTHER PUBLICATIONS

Takara Belmont 50-page Japanese language dental equipment catalog, cover and p. 47, circa Jan. 1991.
A-Dec 117-page equipment catalog, cover and pp. 21-38, Jan. 1991.
Signo "Grand" 19-page Japanese language brochure, cover, pp. 17-18, circa Jan. 1991.
KaVo "Estetica ® 1042 Die Faszination des Fortschritts" German language 13-page brochure, pp. 1-2, Jan. 1991.
A-Dec 121-page catalog, cover and p. 101, circa Sep. 1991.
Robin Dental Company 40-pg. catalog, cover and p. 29, Feb. 1985.
Osada "FX Series" 31-page Japanese language brochure, cover and p. 23, circa Jan. 1991.
Dentech 32-page catalog, cover and p. 22, circa Jan. 1991.
J. Morita Corporation "Surpass" 21-page Japanese language brochure, cover and p. 20, circa Jan. 1991.
Elan 2000 III 20-page Japanese language catalog, cover and p. 15, circa Jan. 1991.
Syntex "Star-Flex Oral Opticl Handpiece" six-page brochure, circa Jan. 1985.
Demetron "Microlux" seven-page installation manual, circa Jan. 1981.
Demetron "Microlux" two-page advertisement, circa Jan. 1981.
Demetron "Microlux" four-page price list and specification drawings, circa Jan. 1981.
Dental Electronic "DE" two-page advertisement circa Jan. 1991.
Ritter-Midwest "Power Optic Lighting System" four-page brochure, circa Aug. 1983.
Kinetic Instruments two-page handpiece advertisement, circa Jan. 1991.
KaVo Super-Torque ® Lux "Light" Turbine four-page brochure, Jul. 1982.
VTI "The Master" two page brochure, circa Jan. 1991.

Primary Examiner—Gene Mancene
Assistant Examiner—Nicholas D. Lucchesi
Attorney, Agent, or Firm—Klarquist Sparkman Campbell Leigh & Whinston

[57] ABSTRACT

The service life of a lamp used with a dental handpiece light is enhanced by the brightness control system, which provides a reduced lamp intensity during the time the handpiece is moved from its holder. The control system increases the lamp to its full intensity when the handpiece is actuated.

14 Claims, 4 Drawing Sheets

BRIGHTNESS CONTROL SYSTEM FOR DENTAL HANDPIECE LIGHT

TECHNICAL FIELD

This invention pertains to lights that are incorporated into dental handpieces, and particularly to systems for automatically controlling the brightness of such lights.

BACKGROUND INFORMATION

Conventional dental handpieces include a rigid handle that terminates in a head that houses a pneumatically driven turbine. High-pressure operating air is coupled to the handpiece. Actuation of the handpiece causes the high-pressure air to be directed to the head for driving the turbine. A bur or drill connects to the turbine to rapidly rotate as the turbine is driven. The handpiece is also connectable to a source of water so that cooling water may be ejected from the head as the drill is used in a conventional dental procedure.

In the past, lights have been connected to dental handpieces for illuminating the work area inside the dental patient's oral cavity. One way of providing the illumination is to mount a high-brightness lamp within the coupled end of the handpiece (that is, the end of the handpiece away from the head), and to transmit the light through the handpiece via a fiber optic component that terminates near the head of the handpiece. Light emitting from the terminus of the fiber optic component illuminates the work area.

Proper illumination, and the accurate rendition of tissue colors, requires a handpiece light that provides the very bright or "white" light that is available from conventional tungsten-halogen lamps.

Tungsten-halogen lamps are relatively expensive and, like other incandescent lamps, have a limited service life. Accordingly, designs in the past have provided mechanisms that tend to conserve the service life of the lamp and make it easy to replace a used lamp. For example, the activation of the handpiece light may be coupled to actuation of the handpiece so that the light is on only when the handpiece is used. When the handpiece is stopped, the lamp will typically remain illuminated for a brief period so that the light can be used for further inspection. After that delay period, the lamp is automatically turned off.

SUMMARY OF THE INVENTION

This invention is directed to a handpiece light, and particularly to a system for automatically controlling the brightness of a lamp that is used with a handpiece light, thereby to conserve lamp service life. The effect of the control is to provide a handpiece light that illuminates with full intensity only when the handpiece is actuated to drive the turbine but otherwise illuminates at a reduced intensity whenever the handpiece is held, such as when used as an inspection tool, but the turbine is not driven.

In a preferred embodiment, the brightness control functions in combination with a switching mechanism that is mounted in the handpiece holder. Whenever the handpiece is removed from its holder, the lamp is illuminated at the reduced intensity. The control system extinguishes the lamp whenever the handpiece is returned to the holder.

When the held handpiece is actuated (for example, through operation of a foot-actuated switch for delivering the high-pressure air to the turbine) the brightness control causes illumination of the lamp to full intensity, thereby enhancing the view of the work area during the time the handpiece is actuated. Full lamp intensity is desirable during such operation of the handpiece because the dentist's view tends to be partly obscured by coolant water or mist that is projected from the handpiece head during operation.

It has been found that the dual lamp-intensity provided by the brightness control of the present invention greatly enhances the lamp service life. The reduced intensity of the lamp is sufficient for providing illumination of the work area with a barely noticeable difference as compared to the full intensity illumination that occurs when the handpiece is actuated.

DETAILED DESCRIPTION OF A PREFERRED EMBODIMENT

Figure 1:
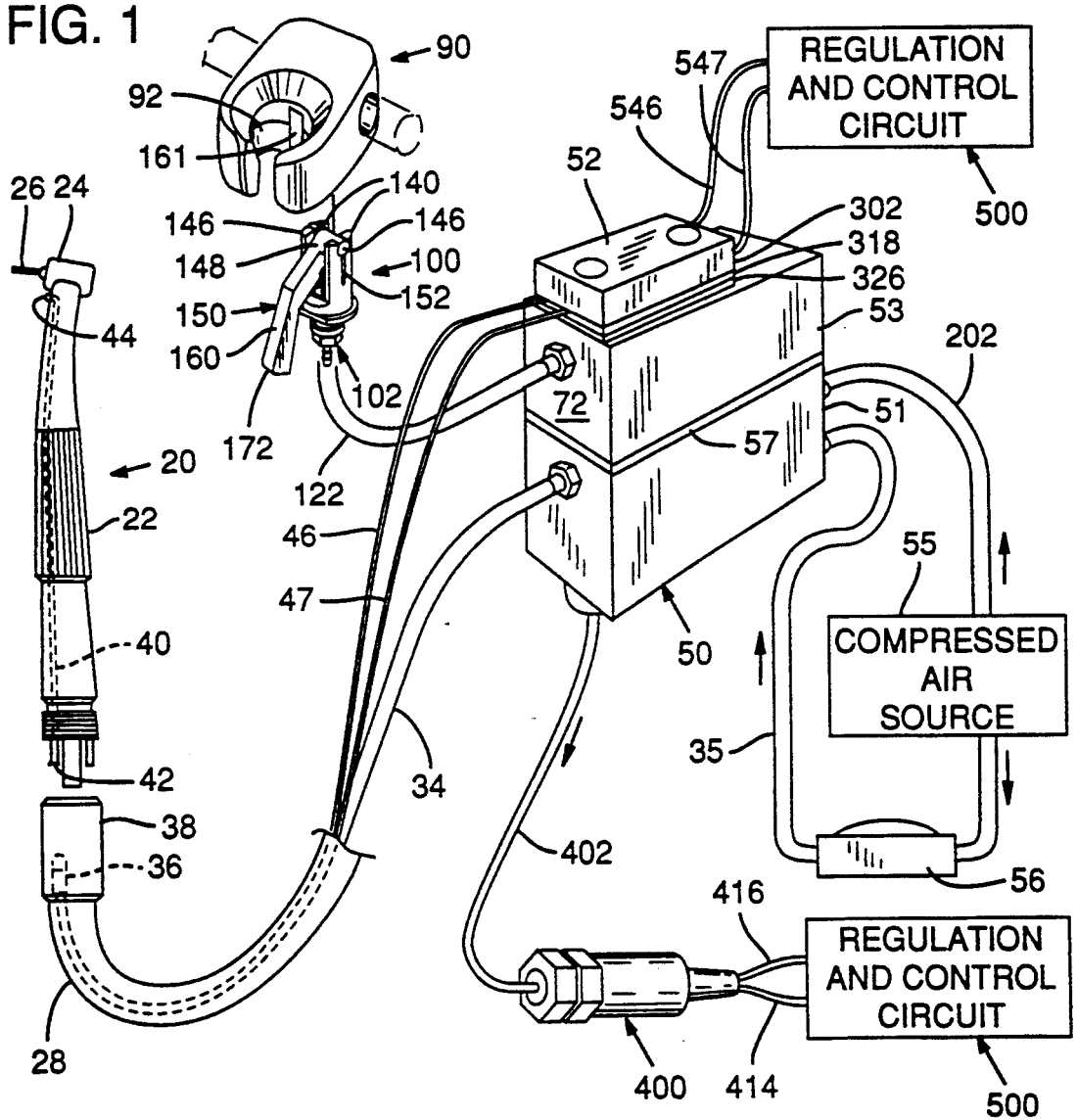
FIG. 1 is a diagram showing a dental handpiece in conjunction with the components of the handpiece light brightness control system of the present invention.

The brightness control system of the present invention may be used with a conventional dental handpiece, such as depicted at 20 in FIG. 1. The handpiece includes an elongated handle 22 that terminates at one end in a head 24 in which is housed a turbine. A bur 26 is connected to the turbine.

The handpiece handle 22 is coupled at its opposite end to a flexible tube 28. The tube 28 encloses a discrete conduit 34 that conducts high-pressure (approximately 35 psi) drive air for operating the handpiece turbine. Air coolant and water coolant conduits are also carried within the tube 28, but for the purpose of clarity, only the drive air conduit 34 is depicted in the figure.

A tungsten-halogen type high-brightness lamp 36 is carried within a socket that is mounted within the coupling 38 at the end of the tube 28. A conventional, elongated fiber optic component 40 is carried in the handle. When the handpiece 20 is coupled to the tube 28, the lamp 36 contacts an end 42 of the fiber optic component 40. When the lamp 36 is illuminated, as described below, light from the lamp propagates through the component 40 and emanates from the outer end 44 of the component, which end is mounted to the handpiece handle to illuminate the region near the bur 26. The two electrical leads 46, 47 from the socket of lamp 36 are also carried within the tube 28 and connect with a handpiece select switch 52, as described below.

The handpiece 20 is actuated (that is, high-pressure drive air is directed through the handpiece to drive the turbine in head 24 for rotating the bur 26) by mechanisms described next. The drive air conduit 34 is connected between the handpiece 20 and a handpiece control block 50. The handpiece control block may be, for example, that described in commonly owned U.S. patent application No. 07/808,946, hereby incorporated by reference. To the top of the block 50 is mounted the handpiece select switch 52, which is also described in detail in the incorporated application.

Figure 2:
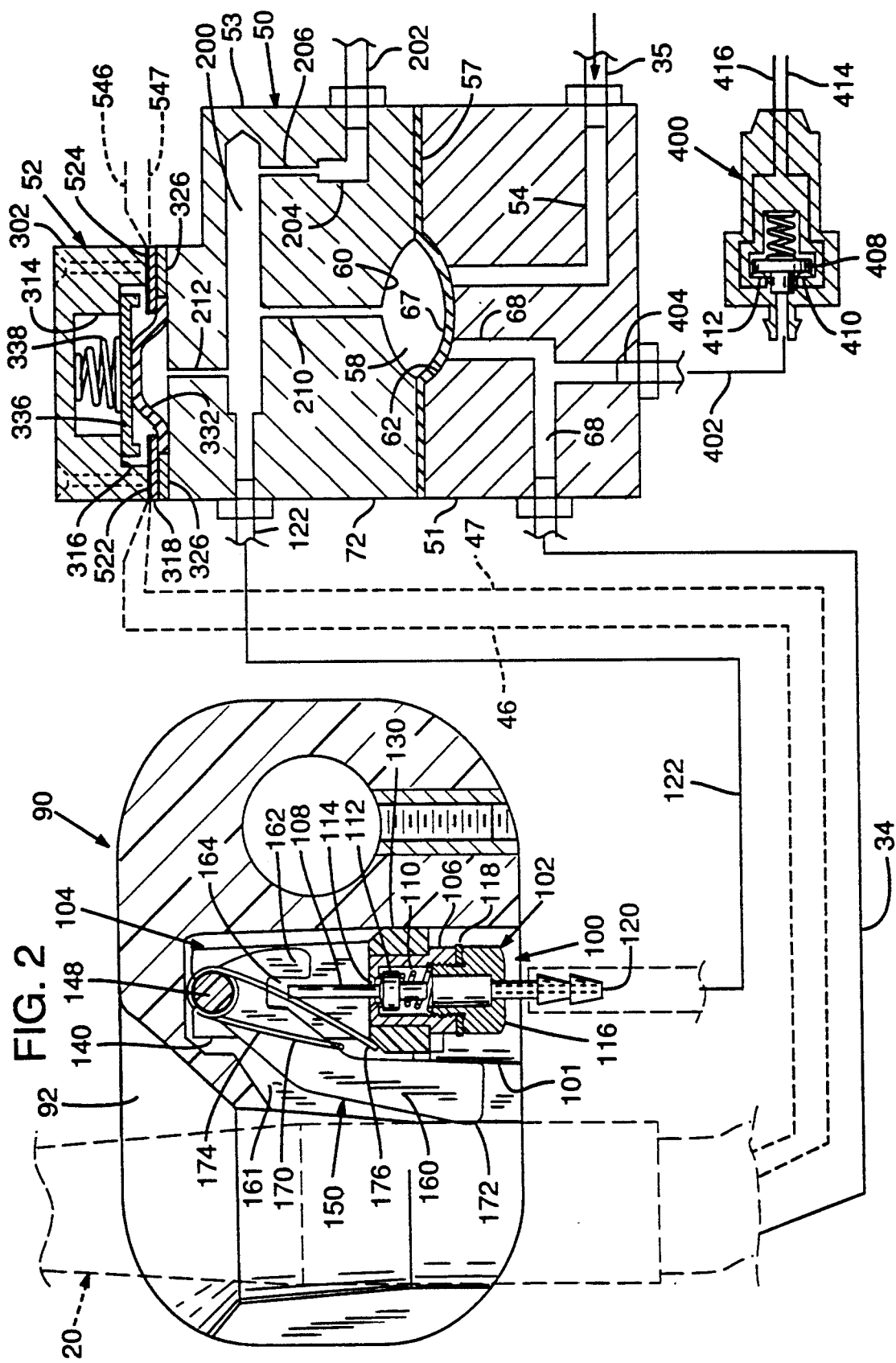
FIG. 2 includes a cross-sectional diagram of a handpiece holder with incorporated switching mechanism, along with a schematic cross-section diagram of a handpiece control block, depicting the system in a state where the handpiece light is off.
Figure 3:
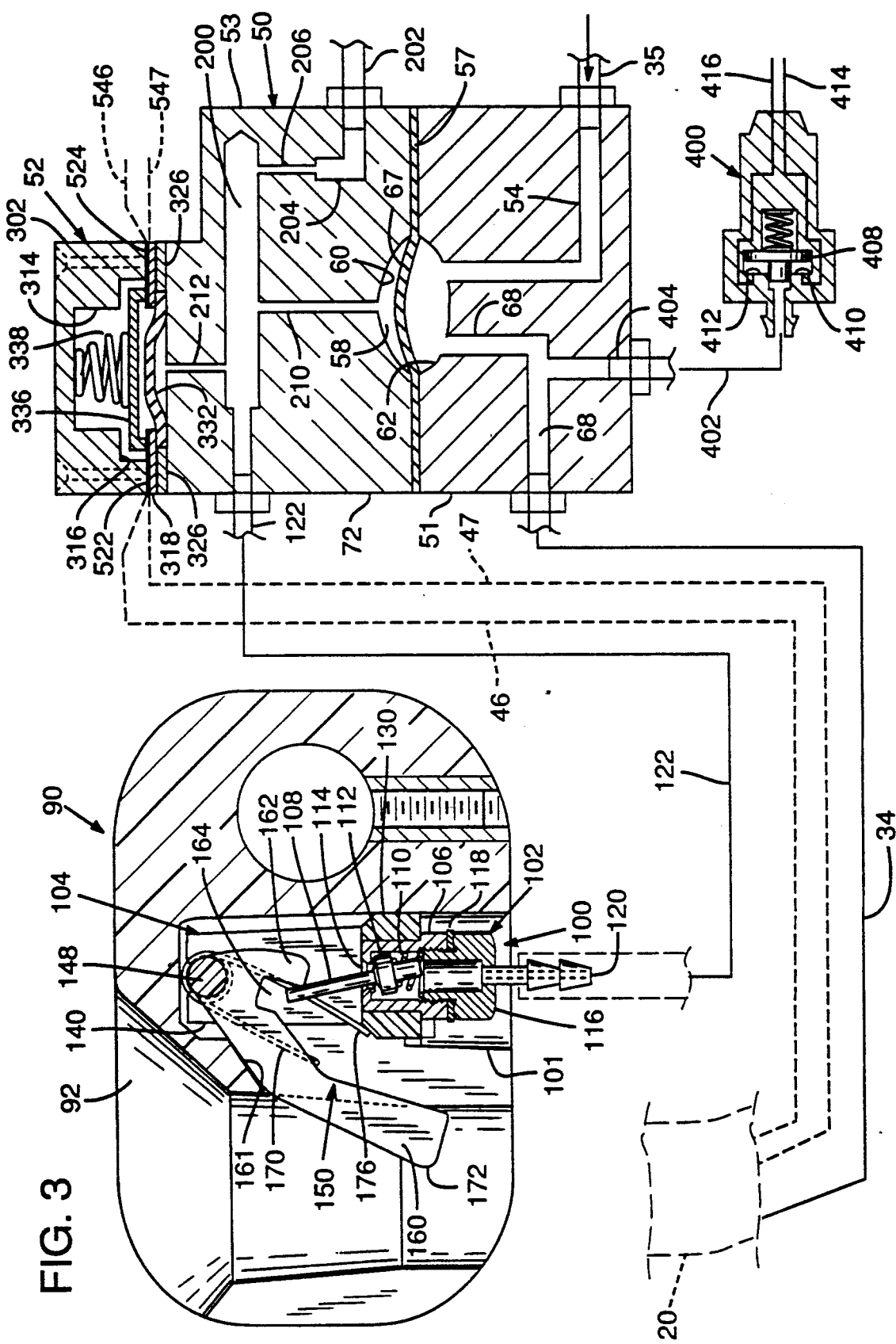
FIG. 3 is a diagram like FIG. 2, depicting the system in a state where the handpiece light is on at full intensity.

The pertinent aspects of the handpiece control block 50 are best shown in the schematic cross-section diagrams of FIGS. 2 and 3. The block 50 generally comprises a base 51 to which is clamped a lid 53. Between the base 51 and the lid 53, there is secured an elastomeric diaphragm 57. These components make up a sealed member having numerous passages for the purpose of providing control of water and air flow to various dental instruments.

More particularly, the control block 50 receives in an inlet passageway 54 high-pressure drive air from a compressed air source 55. The flow of drive air to the inlet passageway 54 is controlled in a conventional manner by a foot-operated valve 56 that is connected between the source 55 and a conduit 35 that leads to passageway 54 (see FIGS. 1 and 2).

The drive air inlet passageway 54 terminates at an internal chamber 58 formed within the control block 50. The chamber 58 is defined by the junction of opposing concave depressions 60, 62 respectively formed in the adjacent surfaces of the lid 53 and base 51 of the control block. The inlet passageway 54 terminates at the concave surface 62 of the chamber 58, adjacent to the terminus of a drive air outlet passageway 68 that extends from the chamber 58 to connect with the drive air conduit 34 at an outer surface 72 of the handpiece control block 50. The other end of the conduit 34, as explained, is connected to the handpiece 20 for delivering drive air to the turbine.

The handpiece is actuated whenever the dentist operates the foot-operated valve 56 to direct the drive air through the inlet passageway 54. The drive air moves through chamber 58, outlet passageway 68, and through the drive air conduit 34 to the handpiece turbine. As will become clear upon reading the following description, the elastomeric diaphragm 57 serves to restrict drive air flow through the chamber 58 whenever a "hold-back" or control air pressure is applied to the upper surface 67 of the diaphragm within the chamber 58 (see FIG. 2). In the absence of the control air pressure, diaphragm 57 is deformable away from the concave depression 62 thereby to place the inlet passageway 54 and outlet passageway 68 in fluid communication for delivering the drive air to the handpiece as just mentioned (See FIG. 3).

The control air is described more fully below by first turning to a description of a switching mechanism carried in the holder 90 in which the handpiece 20 is hung when not in use. The handpiece holder 90 defines an opening 92 that is shaped to receive and hold the handpiece when the handpiece is lowered into the holder opening. A valve assembly 100 is installed within a cavity 101 that is formed in the holder 90 adjacent to the opening. For clarity, FIG. 1 shows the valve assembly 100 out of the cavity 101 in which it is normally installed. The installed orientation of the valve 100 is shown in FIGS. 2 and 3.

The valve assembly 100 generally serves as a pneumatic switching mechanism for indicating when the handpiece is or is not carried in the holder 90. The assembly specifically includes a valve 102 that is secured to a trigger assembly 150 The valve 102 includes a hollow cylindrical body 106 that contains the base 112 of a valve stem 108. The stem 108 is forced by an internal spring 110 into coaxial alignment with an opening 114 in the body 106 so that the base 112 of the stem 108 normally occludes the opening 114 The valve body 106 is closed on the bottom by a nut 116 and washer 118. A connector 120 is fastened to the nut 116 and provides fluid communication between the interior of the valve body 106 and a control air line 122 that is connected at one end to the valve body 106 and, at the control block surface 72, to a pressurized control-air passageway 200 formed in the block, and described more fully below.

When the valve stem 108 is in its closed position, FIG. 2, the base 112 of the stem seals the opening 114 in the valve body so that no air will bleed from the connected control air line 122. Whenever the stem 108 is tipped out of the closed position, such as shown in FIG. 3, the base 112 of the valve stem shifts by an amount sufficient to let air bleed from the control line 122 through the open valve 102, the effect of which is described below.

The trigger mechanism 150 is mounted to the holder 90 for opening the valve 102 in response to the removal of the handpiece 20 from the holder, and for closing the valve whenever the handpiece is returned to the holder.

The trigger mechanism 150 includes a base 130 through which is formed a hole, into which hole tightly fits the body 106 of the valve 102 (FIGS. 1 and 2). The bottom of the valve body 106 is flanged to abut the undersurface of the base 130.

A pair of spaced apart pivot brackets 140 extend upwardly from the base 130 of the trigger mechanism. The upper portion of each pivot bracket 140 includes a rounded groove into which groove snap-fits a cylindrical end 146 of a pivot post 148 that is integrally formed with the trigger arm 160 of the trigger mechanism 150. A slit 152 (FIG. 1) is formed to extend Contiguously from each groove through a portion of each bracket 140 so that the groove portion near the uppermost ends of the brackets 140 can enlarge slightly as ends 146 of the pivot post 148 are pressed into the grooves during assembly of the trigger mechanism 150.

The trigger mechanism 150 includes an elongated trigger arm 160 protruding from the center of the pivot posts 148 in a direction generally outwardly and downwardly from the post 148. At the junction of the arm 160 and pivot post 148, the trigger is shaped to define a downwardly protruding boss 162. A clearance space 164 is defined between the arm 160 and boss 162, into which space the stem 108 of the valve 102 extends between the brackets 140.

A spring 170 is attached to the trigger 150 to normally urge the tip 172 of the arm outwardly, away from the valve 102. The spring 170 (FIG. 2) is coiled to fit over one of the cylindrical ends 146 of the pivot post 148. One leg 174 of the spring has a bent end that fits against the trigger arm 160. The other leg 176 of the spring bears against a sloped surface formed in the base 130 between the lower portions of the brackets 140. When the valve assembly 100 is assembled, the spring legs 174, 176 are normally urged apart for forcing the arm 160 away from the base 130 as shown in FIG. 3.

The valve assembly 100 is installed within the cavity 101 of the instrument holder so that the trigger arm 160 fits through a slot 161 (FIG. 1) formed in the holder to extend between the opening 92 and the cavity 101 for permitting the tip 172 of the arm 160 to protrude into the opening 92.

With reference to FIG. 3, it will be appreciated that when there is no handpiece present in the opening 92 of the holder 90, the trigger arm 160 protrudes as shown and the boss 162 is swung by the action of the spring 170 against the stem 108 to move the stem into the open position shown. The top wall of the holder slot 161 acts as a stop to limit the outward extension of the trigger arm 160. Whenever a handpiece is reinserted into the holder opening 92, as shown in FIG. 2, the arm 160 is pushed into the slot 161 and, therefore, the boss 162 rotates away from the stem 108 so that the stem can resume the upright, closed position and fit within the clearance space 164 between the trigger arm 160 and the boss 162.

In view of the foregoing, it will be appreciated that the handpiece holder 90 and valve assembly 100 as just described provides a very compact and easily assembled mechanism. The assembly 100 can be manufactured as essentially a self-contained unit that is easy to install into the holder.

As noted, the control air line 122 places the valve 102 in fluid communication with a control air passageway 200 formed in the control block. The control air passageway is continuously fed pressurized air (for example, 80 psi) from the compressed air source 55 via an air line 202 that leads to a control block passageway 204. That passageway 204 includes a very small (for example 0.005 inch) bleed orifice 206 that connects that passage 204 to the control air passageway 200.

Whenever the handpiece 20 is placed within the holder 90 (hence, whenever valve 102 is closed), the pressure within control air passageway 200 is maintained (that is, the pressure in the passageway does not drop as a result of the air bleed from valve 102 that would occur if the handpiece were not in the holder 90). The control air pressure in passageway 200 is communicated through a port 210 to the chamber 58, thereby acting upon the surface 67 of the elastomeric diaphragm 57 to deflect that diaphragm against the concave depression 62 and prevent communication between the inlet drive air passageways 54 and the outlet passageway 68.

The pressure in the control air passageway 200 is also communicated via a port 212 to the handpiece select switch 52 that is mounted to the control block 50. As will be described more fully below, the control air pressure is normally sufficient for opening the handpiece select switch FIG. 2), the open handpiece select switch indicating, therefore, that the handpiece 20 is held within the holder.

Whenever the handpiece 20 is removed from the holder, the above-mentioned spring-biased trigger mechanism 150 opens the valve 102, thereby to bleed via tube 122 control air from passageway 200. The rate of airflow bled from the passageway 200 is much greater than the inflow of the control air through the constricted orifice 206. As a result, the pressure drop in passageway 200 permits the closing of the pressure-operated handpiece select switch. Moreover, the pressure drop in passageway 200 has the effect of opening fluid communication between the drive air inlet passageway 54 and the outlet passageway 68 by permitting the elastomeric diaphragm 57 to deform away from those passageways within the chamber 58 (FIG. 3). In short, whenever the handpiece is removed from the holder, drive air may be directed to the handpiece 20 (through actuation of the foot-operated valve 56), and the handpiece select switch closes.

Turning to the particulars of the handpiece select switch 52, that switch is mounted by screws, (not shown) to the top of the control block 50 and comprises a generally rectangular top part 302 formed of non-conductive material. The top part 302 is formed with a cylindrical, counterbored recess 314 in its undersurface, the recess being centered over the port 212. The counterbored recess 314 defines a downwardly facing annular shoulder 316. Secured to the underside of the top part 302 is a circuit board 318 formed of insulating material and having a central opening concentric with the cylindrical recess 314 and having a diameter no greater than about the inner diameter of the shoulder 316.

Secured to the upper surface of the circuit board 318 are the termini of the leads 46, 47 that extend to the handpiece lamp 36. One lead 47 is made contiguous on the board 318 with another lead 547 that exits the switch 52 is applied to a regulation and control circuit 500 as described below. The other lead 46 terminates in one conductor 522 of a pair of conductor elements 522, 524 having facing, spaced apart semi-annular end portions concentric with the recess 314. The other conductor element 524 connects with a lead 546 that is connected to the hereafter described regulation and control circuit 500.

Secured to the lower surface of the circuit board 318 is a spacer board 326 having an opening concentric with the recess 314. The brim of a hat-shaped elastomeric diaphragm 332 is sealed against the spacer board 326 and the underside of the circuit board 318. The diaphragm 332 is positioned concentric with the recess 314.

Positioned within the recess 314 beneath the shoulder 316 is a cup-shaped connector element 336 formed of conductive material. Positioned above the connector element 336 is a coil spring 338, which biases the connector element downwardly toward the conductor elements 522, 524.

Alternatively, the combination of the diaphragm 332 and spacer board 326 could be replaced with a single generally flat resilient diaphragm. Between such a diaphragm and the connector element 336 is a non-conductive disc or puck for moving the element 336 as the diaphragm deforms.

Whenever the handpiece is removed from the holder 90 so that the control air in passageway 200 is bled to atmosphere via the opening of the holder valve 102, the spring 338 forces the connector element 336 into contact with the conductor elements 522, 524 (FIG. 3). When the handpiece is within the holder opening 92, the pressure within the passageway 200, against the diaphragm 332 forces the diaphragm upwardly so as to move the connector element 336 out of contact with the conductor elements 522, 524 to open the circuit between them (FIG. 2).

In an alternative embodiment, the connector element portions that contact the conductor elements may be configured as spring-like members having contact surfaces inclined relative to the surface of the board so that those portions deflect somewhat to wipe across the contact surface of the elements 522, 524 as the connector element comes into contact with the conductor elements.

The handpiece select switch 52 is connected via the pair of leads 546, 547 to the regulation and control circuit 500 for conveying the opened and closed state of the handpiece valve 100 (or "switch"), as described more fully below.

A dimmer switch 400 is incorporated into the present control system for the purpose of providing an indication of when the handpiece is actuated; that is, when the turbine is or is not driven. The indication of handpiece actuation is detected by the regulation and control circuit 500 for the purpose of increasing or decreasing the voltage applied to the handpiece lamp 36, thereby varying the intensity of the handpiece light.

The dimmer switch 400 may be any suitable pressure transducer operable for opening and closing an internal switch in response to changes in drive air pressure. In the present system, the dimmer switch 400 is connected via a conduit 402 to a passageway 404 formed in the control block 50. That passageway intersects the outlet drive passageway 68. Passage 404 therefore, directs air from the outlet passage 68 whenever the drive air is applied to the handpiece turbine via operation of the foot-actuated valve 56 as described above. This air is conducted, therefore, via conduit 402 to the normally-closed dimmer switch.

The air pressure is sufficient for displacing from its normal positioning (FIG. 2) a moveable conductive contact 408 that electrically joins the termini 410, 412 of the two leads 414, 416 of the dimmer switch. That moveable contact 408 is normally held in the closed position (thereby closing the circuit between the leads 414, 416 by a resilient member, such as a spring or diaphragm). FIG. 3 schematically depicts the dimmer switch in the open state wherein the pilot air 402 has displaced the contact member 408, thereby opening the circuit between the switch leads 414, 416.

Figure 4:
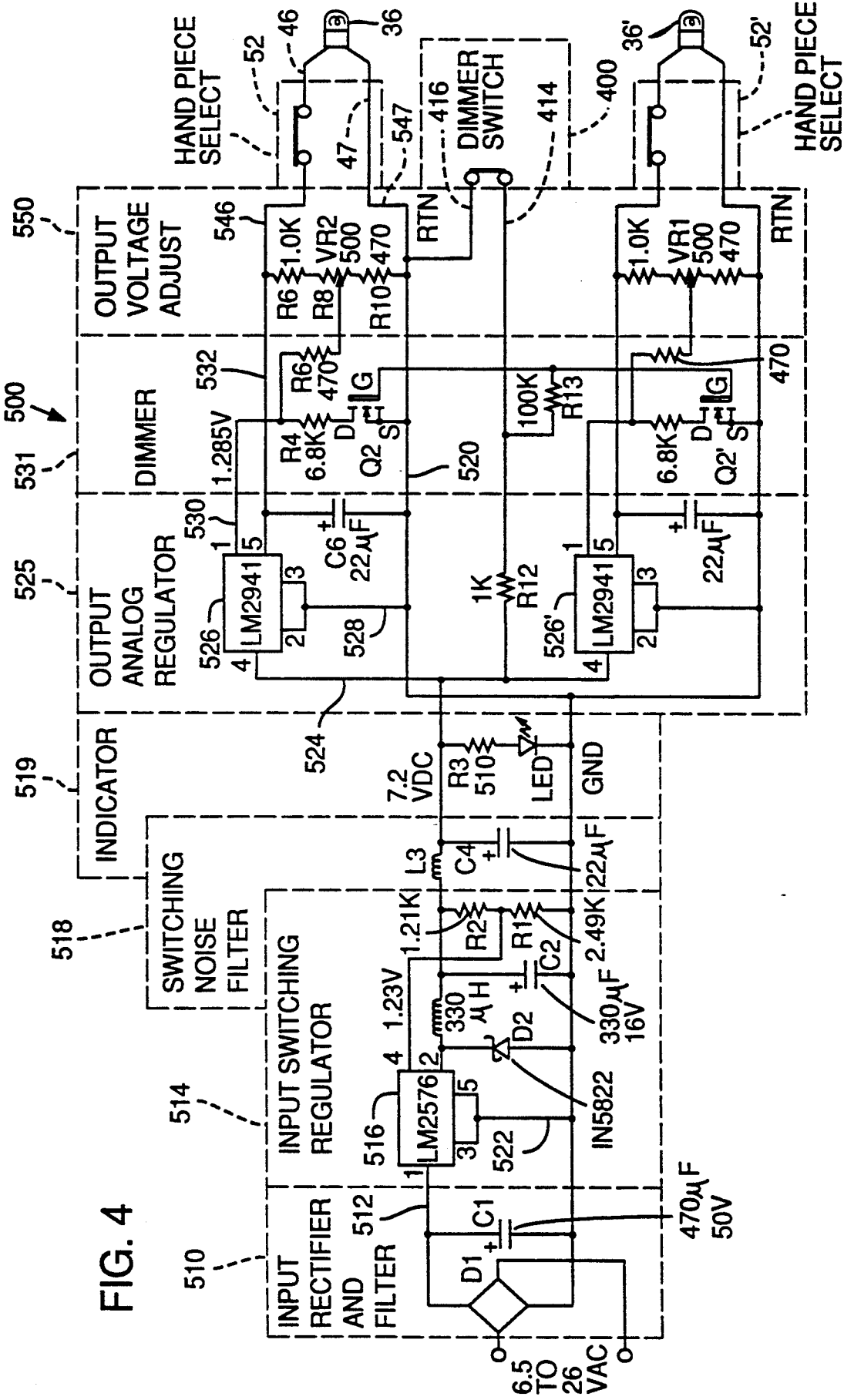
FIG. 4 is a schematic diagram of a regulation and control circuit of the present system.

Turning now to the particulars of the regulation and control circuit 500, and with reference to FIG. 4, it is initially noteworthy that the circuit components are selected for providing the required regulation with a compact package having low heat dissipation requirements. The circuit 500 permits regulation of power to at least two handpieces. Moreover, the circuit is operable for regulating a somewhat high input voltage for controlling a lamp with correspondingly high voltage requirements (for example, 6 volts). The same circuit 500 is also operable for controlling a relatively low voltage lamp (for example 3 volts) with little internal heat generated despite the use of the relatively high input voltage.

The input rectifier D1 and filter (capacitor C1) smooths the DC voltage that is input to the switching regulator 514. That regulator comprises a National Semiconductor type LM2576 integrated circuit that provides a switching regulator package that converts the DC input (pin 1) with approximately 80% efficiency to 7.2 volts on the output (pin 2). This high efficiency regulation accommodates a wide voltage range on the output (depending upon lamp requirements) with low heat dissipation requirements.

Diode D2 serves as a flyback diode, and the coil L1 is an energy storage coil for smoothing the DC output switching pulses, along with the output filter capacitor C2. Resistors R2 and R1 form feedback divider for setting the proper feedback voltage (nominally 1.23 volts) for maintaining the output of the switching regulator 516 at 7.2 volts.

The switching noise filter 518, comprising L2 and C4, provide an additional smoothing network to eliminate high-frequency noise residue from the switching supply. The power indicator 519, comprising R3 and the LED, are located in the circuit where a very stable DC voltage is present so that LED brightness is correspondingly stable.

The output of the regulator 514 is available on line 524 to provide two channels for regulating voltage to two discreet handpiece lamps. Accordingly, components of the second channel that are identical to those of the next-described first channel are shown with a prime indicia in FIG. 4.

The voltage applied on line 524 is input to an analog regulator 526 component of the output analog regulator circuit portion 525. The regulator 526 is, preferably, a National Semiconductor type LM2941 employing PNP-type transistors, thereby minimizing voltage drop across regulator. Accordingly, the regulator 526 can provide a 6 volt output using the 7.2 volts DC input. Typical NPN-type regulators would require at least 9 volts on the input for providing the same output. Accordingly, regulator 526 provides a contribution to the low heat-dissipation feature of present circuit.

The output voltage of the regulator 526 is applied to line 532, the level of that output voltage being a function of the feedback voltage provided at pin 1 of the regulator 526 via line 530. The feedback voltage is set by the divider network R8, VR2, and R10. The inclusion of the potentiometer VR2 makes the divider adjustable (portion 550 of the circuit) for setting the nominal operating voltage of the lamp from about 3.5 volts to about 6 volts. Moreover, the inclusion of another, independently operated potentiometer VR1 in the second channel permits independent voltage adjustment for lamps 36 and 36', thereby allowing a single regulation and control circuit to operate with different lamps having different voltage requirements.

The feedback voltage on line 530 is also modified with the dimmer network 531, comprising R6 and R4 and Q2, the transistor Q2 acting as a switch. The dimmer network 531 is responsive to the dimmer switch 400 for depleting (when dimmer switch 400 is closed) the nominal feedback voltage to regulator 526, which depletion has the effect of increasing or maximizing the output on line 532 to increase the illumination intensity of lamp 36. Specifically, whenever Q2 is off, the line to R4 is effectively open circuited. When Q2 is on, the line to R4 is effectively shorted to the return line 520.

In this regard, whenever the dimmer switch 400 is open (which occurs whenever the handpiece is actuated) R13 pulls the gate at Q2 high, and Q2 turns on to short the line to R4 to the return line 520, hence reducing the feedback voltage on line 530. Consequently, the output of the regulator 526 moves to its high state in order to compensate for the feedback reduction. Accordingly, the lamp brightens when the dimmer switch 400 is opened.

Whenever the dimmer switch 400 is closed. The node of R13 is held to the return line 520, thereby placing the gate potential of Q2 low. The transistor Q2, therefore, opens (i.e., has high impedance) to effectively short the line to R4 out of the circuit, so that the full feedback voltage on line 530 from the divider is applied to the regulator 526. As noted, the full feedback voltage switches the output of the regulator 526 to the low state to dim the lamp 36.

Preferably, the values of R6 and R4 are selected so that the divider effect of these resistors that occurs when the dimmer switch is opened (i.e., when Q2 is on) will reduce the nominal feedback voltage by about 13%. This 13% reduction has the effect of increasing the output voltage on line 532 by a corresponding 13%. It will be appreciated that any number of such divider ratios may be employed.

The adjusted output of the regulator 526 is applied to a lead 546 of the handpiece select switch 52. As described, whenever the handpiece 20 is removed from the holder 90, the switch 52 is closed for directing the output to the lamp 36.

It will be appreciated that any of a multitude of electronic component arrangement can be substituted for the foregoing circuit as described and illustrated for the purpose of achieving the dual-intensity feature that is an aspect of the present invention.

While the present invention has been described in accordance with preferred embodiments, it is to be understood that substitutions and alterations may be made thereto without departing from the spirit and scope of the appended claims.

The invention claimed is:

1. An assembly for controlling the brightness of a dental handpiece light, comprising:
   a holder for holding the handpiece until the handpiece is removed from the holder by a user;
   handpiece drive means operable by the user for directing operating fluid to the handpiece;
   a first switch connected to the holder which switches from a first state to a second state when the handpiece is removed by the user;
   a second switch connected to the handpiece drive means which switches from a first state to a second state when the user directs operating fluid to the handpiece; and
   control means for applying to the light a first voltage in response to the first switch switching to its second state, and for applying to the light a second voltage that is greater than the first voltage in response to the second switch switching to its second state while the first switch is in its second state.

2. The assembly of claim 1 wherein the control means is functional for reducing the second voltage to the first voltage in response to the second switch switching to its first state while the first switch is in its second state.

3. The assembly of claim 1 wherein the control means is functional for removing the application of the first voltage in response to the first switch switching to its second state.

4. The assembly of claim 1 further comprising adjustment means for varying the level of the second voltage.

5. The assembly of claim 1 further comprising a second control means for applying to a second light a third voltage that is increased to a fourth voltage in response to the second switch switching to the second state.

6. The assembly of claim 5 further comprising second adjustment means for varying the level of the fourth voltage independently of the level of the second voltage.

7. A method of controlling the brightness of a light that is carried on a dental handpiece, wherein the handpiece may be switched by a user into and out of an actuated state, and wherein pressurized fluid is applied to the handpiece when the handpiece is in the actuated state, the method comprising the steps of:
   applying a first voltage to the light when the handpiece is out of the actuated state; and
   increasing the first voltage to a second voltage in response to the user switching the handpiece into the actuated state.

8. The method of claim 7 further comprising the step of reducing the second voltage in response to the user switching the handpiece out of the actuated state.

9. The method of claim 8 wherein the handpiece is removably held in a holder when not in use and wherein the reducing step includes the steps of reducing the second voltage to the first voltage in response to the user switching the handpiece out of the actuated state, and maintaining the application of the first voltage when the handpiece is removed from the holder.

10. The method of claim 7 wherein the handpiece is removably held in a holder when not in use, the method further comprising the step of applying the first voltage to the light whenever the handpiece is removed from the holder.

11. The method of claim 10 further comprising the step of removing any voltage applied to the light whenever the handpiece is returned to the holder.

12. The method of claim 7 further comprising the step of providing adjustment means for varying the level of the second voltage.

13. The method of claim 7 further comprising the step of applying the second voltage to a second light.

14. The method of claim 13 comprising the step of providing second adjustment means for varying the level of the second voltage applied to the second light independently of the level of the second voltage applied to the first-mentioned light.

* * * * *